(12) United States Patent
Van Eupen

(10) Patent No.: US 8,686,153 B2
(45) Date of Patent: Apr. 1, 2014

(54) LENALIDOMIDE SALTS

(75) Inventor: Jacobus Theodorus Henricus Van Eupen, Nijmegen (NL)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 13/390,204

(22) PCT Filed: Aug. 12, 2009

(86) PCT No.: PCT/EP2009/006857
§ 371 (c)(1),
(2), (4) Date: Apr. 13, 2012

(87) PCT Pub. No.: WO2011/018101
PCT Pub. Date: Feb. 17, 2011

(65) Prior Publication Data
US 2012/0190711 A1  Jul. 26, 2012

(51) Int. Cl.
*C07D 401/00* (2006.01)
(52) U.S. Cl.
USPC .......................................... 546/200
(58) Field of Classification Search
USPC .......................................... 546/200
See application file for complete search history.

(56) References Cited

U.S. PATENT DOCUMENTS 5,635,517 A    6/1997  Muller et al.
6,281,230 B1 *  8/2001  Muller et al. ................. 514/323

FOREIGN PATENT DOCUMENTS

| WO | WO 2005/023192 | | 3/2005 | |
| WO | 2006028964 | * | 3/2006 | |
| WO | WO 2006/028964 | * | 3/2006 | ........... C07D 209/46 |
| WO | WO 2009/111948 | | 9/2009 | |
| WO | WO 2009/114601 | | 9/2009 | |

OTHER PUBLICATIONS

Serajuddin, Adv Drug Deliv Rev. Jul. 30, 2007;59(7):603-16.*
Tran et al., Expert Opin Drug Deliv. May 2010;7(5):647-61.*

* cited by examiner

*Primary Examiner* — Nizal Chandrakumar
(74) *Attorney, Agent, or Firm* — Mark R. Buscher

(57) ABSTRACT

The present invention relates to acid addition salts of lenalidomide, wherein said acid has a pKa lower than 1, preferably selected from hydrochloric acid, hydrobromic acid, methane sulfonic acid, ethane sulfonic acid, benzene sulfonic acid and p-toluenesulfonic acid, to processes for their making, and use in medicine, and to purification of lenalidomide base.

6 Claims, No Drawings

LENALIDOMIDE SALTS

BACKGROUND OF THE INVENTION

The present invention relates to acid addition salts of lenalidomide, pharmaceutical compositions containing the salts, and methods of purifying lenalidomide base using the salts.

Lenalidomide=3-(4-amino-1-oxo-3H-isoindol-2-yl)piperidine-2,6-dione is a pharmaceutically active compound useful for the treatment of some blood diseases such as multiple myeloma or myelodysplasic syndrome and is represented by the formula (I).

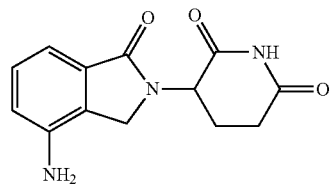

The compound of formula (I), unless stated otherwise, is a racemic compound.

The marketed pharmaceutical composition is an immediate release capsule sold under the brand name REVLIMID® (by Celgene), that contains lenalidomide as a hemihydrate of the free base. Lenalidomide was first described in U.S. Pat. No. 5,635,517 and was generically described as including salts thereof, but no actual salt of lenalidomide was shown.

Lenalidomide is a poorly water soluble compound with the highest solubility in 0.1N HCl (18 mg/ml) and lower solubility at pH 4.6, 6.8 and 7.4 (0.4-0.5 mg/ml).

While the commercially useful lenalidomide free base form is a hemihydrate, a patent application WO 2005/023192 describes 8 forms of lenalidomide base: three unsolvated forms, the hemihydrate, a dihydrate, an acetone hemisolvate, an acetonitrile solvate, and a dehydrated form of the dihydrate. However, nothing is known whether and under which conditions lenalidomide may form isolatable acid addition salts and an improvement in this respect is desirable.

Processes for making lenalidomide were disclosed in U.S. Pat. No. 5,635,517, WO2006/028964 and WO2005/005409. In general, these processes involve a cyclization and reduction steps. These processes are apparently accompanied by the formation of impurities but no purification process has been disclosed. It would be therefore desirable to have purification techniques for preparing lenalidomide of a high purity, particularly lenalidomide of a pharmaceutical grade.

SUMMARY OF THE INVENTION

The present invention relates to the discovery of stable acid addition salts of lenalidomide that are useful for the purification of lenalidomide base as well as in pharmaceutical compositions.

Accordingly, a first aspect of the invention relates to an acid addition salt of lenalidomide, wherein said acid has a pKa lower than 1. The acid can be preferably selected from hydrochloric acid, hydrobromic acid, methane sulfonic acid, ethane sulfonic acid, benzene sulfonic acid and p-toluenesulfonic acid. The solid state form of these salts is preferred and includes crystalline as well as amorphous states. Typically the solid state lenalidomide acid addition salt is a monovalent salt having an acid:base ratio of about 1:1. Advantageously, the lenalidomide acid additional salt is selected from lenalidomide benzenesulfonate and lenalidomide p-toluenesulfonate, preferably from crystalline lenalidomide benzenesulfonate and crystalline lenalidomide p-toluenesulfonate.

Yet another aspect of the present invention relates to a process of making an acid addition salt of lenalidomide, which comprises combining lenalidomide base and an acid having a pKa lower than 1 in a solvent, preferably a polar solvent and most preferably in a water-alcohol solvent, to form a solution; precipitating a lenalidomide acid addition salt from said solution; and optionally isolating the precipitated lenalidomide acid addition salt.

A further aspect of the present invention relates to a process of purifying lenalidomide base, which comprises converting lenalidomide into an acid addition salt of lenalidomide with an acid having a pKa lower than 1 in a solvent, preferably a polar solvent; optionally isolating the acid addition salt; converting the lenalidomide acid addition salt into purified lenalidomide base.

Another aspect of the present invention relates to a pharmaceutical composition comprising the lenalidomide acid addition salt described above and at least one pharmaceutically acceptable excipient.

Still another aspect of the invention relates to the use of the lenalidomide acid addition salts described above for use in medicine, such as treatment of blood diseases, and for purification of lenalidomide.

DETAILED DESCRIPTION OF THE INVENTION

The molecule of lenalidomide has one basic centre, particularly the primary amino-group attached on the position 4 of the isoindolone ring. While, in theory, a primary amino group of an amine allows for various types of salts, it was found out that the basicity of the amino group in this particular position is very low and the ability of this group to bind with an acid to form an isolatable salt is very limited. Consequently, it was found out that such salts may be formed only if the acid used for making these salts is quite strong. Thus, the number of actually useful acids for making isolateable salts of lenalidomide is very limited.

The present invention provides various lenalidomide salts that may be isolated from a solution thereof, preferably in a solid state. These acid addition salts are useful for the purification of lenalidomide base and also directly useful in pharmaceutical compositions. An advantage of the acid addition salts of lenalidomide of the present invention is particularly due to their increased solubility in aqueous media. On one hand, this property may be used in purification of lenalidomide, particularly from relatively poorly soluble impurities such as from the nitro-group containing intermediates, as these nitro-compounds cannot form the soluble salts. On the second hand, the improved aqueous solubility of lenalidomide salts of the present invention may be advantageously used in pharmaceutical compositions. The use of a better soluble form of lenalidomide avoids the need of micronization of the lenalidomide material, which is actually necessary in making the Revlimid® capsules employing the poorly soluble lenalidomide base.

The lenalidomide acid addition salts of the invention are made from fairly strong acids having a pKa of about 1 or less, typically about 0 or less. The "pKa" refers to the pKa of the starting acid; hence as used herein reference to the pKa even in the context of the addition salt is referring to the pKa of the starting acid. Suitable acids include, for example, hydrochloric acid, hydrobromic acid, methane sulfonic acid, ethane sulfonic acid, p-toluene sulfonic acid, benzene sulfonic acid and oxalic acid. The pKa values of useful acids may be found, e.g., in Handbook of Pharmaceutical Salts by Stahl P. H. (ed.), Wiley-VCH 2002.

The lenalidomide acid addition salts of the invention are isolatable in a solid state, which can be advantageous. The "solid state" includes crystalline and amorphous forms, as well as mixtures thereof, and also includes solvates and hydrates. Generally the acid addition lenalidomide salts of the invention can be obtained in a stable solid state form making them useful for purification, bulk storage, or use in pharmaceutical compositions and methods of treatment.

Regardless of the fact that the primary amino-group of lenalidomide allows for various types of salts, the lenalidomide acid addition salts of the present invention are typically monovalent salts, i.e., having an acid:base ratio of about 1:1. Analytical methods, such as titration or ionic chromatography, may show a ratio of acid:base of 0.8:1 to 1:1.2 in the isolated solid form of the salt as a result of e.g., traces of unbound acid and/or base and inherent variance associated with the analytical method. Such variation in the acid:base ratio is encompassed by an acid:base ratio of "about 1:1."

Exemplary lenalidomide acid addition salts according to the present invention include lenalidomide hydrochloride, lenalidomide methane sulfonate, lenalidomide benzene sulfonate and lenalidomide p-toluene sulfonate. Each of these salts is isolatable in a crystalline solid state with a molar ratio of lenalidomide to acid moieties of about 1:1.

In general, the exemplary salts are soluble in water, at least in certain extent. For instance, the solubility of lenalidomide benzene sulfonate in water at 20° C. is about 18 mg/ml, the solubility of lenalidomide p-toluene sulfonate in water at 20° C. is about 13 mg/ml. Solubility data were determined using the shaken flask method.

The lenalidomide acid addition salts of the present invention can be made by combining lenlidomide base and an acid having a pKa of 1 or less in a solvent, preferably a polar solvent, to form a solution, and then precipitating a lenalidomide acid addition salt from said solution. Optionally the precipitated lenalidomide acid addition salt can be isolated, e.g., by filtration, as an isolated form. The "isolated form" means a product, which is substantially free from solvents and reagents used in the process of making it, not including any solvent and/or reagent that are firmly bound in a definite amount within the crystalline lattice of the solid material to form specific physical forms such as hydrates, solvates and/or clathrates. In an example, crystalline dimethylformamide solvate of lenalidomide methane sulfonate or of lenalidomide p-toluene sulfonate may be prepared by isolation of the salt from a solvent comprising N,N-dimethylformamide.

The acid useful in the process of making the acid addition salts of lenalidomide of the present invention is typically hydrochloric acid, hydrobromic acid, methane sulfonic acid, ethane sulfonic acid, benzene sulfonic acid and p-toluenesulfonic acid. A molar equivalent or a slight excess of the starting acid with reference to the lenalidomide base is typically used in order to form a lenalidomide acid addition salt having an acid:base ratio of about 1:1.

The lenalidomide base used in forming the lenalidomide acid addition salt (i.e., the starting lenalidomide base) can be any form of lenalidomide base, including a hydrate or a solvate (see, e.g., WO 2005/023192 for examples of such hydrates and/or solvates), in any degree of purity. The starting lenalidomide base can also be crude lenalidomide that is present in the reaction mixtures obtained after the chemical synthesis of lenalidomide.

The solvent used in forming the lenalidomide acid addition salt is typically a polar solvent, which includes both protic and aprotic solvents and/or mixtures thereof. Generally, the dielectric constant of a solvent provides a rough measure of a solvent's polarity; solvents with a dielectric constant of less than 15 are typically considered nonpolar. Examples of suitable polar solvents include water, dimethyl sulfoxide, C3-C10 aliphatic ketones (e.g., acetone, methyl tert.butyl ketone, etc.), C1-C6 aliphatic alcohols (e.g., methanol, ethanol, isopropanol), C2-C5 aliphatic nitriles (e.g., acetonitrile), C3-C10 aliphatic or cyclic amides (e.g., N,N-dimethyl formamide, N,N-dimethyl acetamide) as well as mixtures thereof. Preferred solvents comprise water-alcohol mixtures.

There is no specific order in which the lenalidomide base and the acid must be combined in the solvent to form the solution. Generally the conditions are such that all of the lenalidomide (and all of the acid) is dissolved in the solvent, though strictly speaking such is not required; i.e., some amount of solid or immiscible lenalidomide may be present in the solution. The dissolution of lenalidomide base in the solvent is advantageously performed at an enhanced temperature, which includes a reflux temperature of the solvent. The contacting or combining of the lenalidomide-containing solvent with the acid is advantageously performed at an ambient or higher than ambient temperature, including the reflux temperature of the solvent. In other embodiments, the acid can be added, e.g., substantially at the same time as the base, before the base, etc.

The precipitation of the lenalidomide acid addition salt can be carried out in various ways. For example, the precipitation can occur spontaneously upon the contacting of the lenalidomide with the acid in the solvent. Precipitating of the lenalidomide acid addition salt can also be induced by seeding the solution, cooling the solution, evaporating at least part of the solvent, adding an antisolvent, which advantageously is a liquid, which is less polar than the original solvent, and by combining one or more of these techniques.

The precipitated lenalidomide acid addition salt can be isolated from the solution by conventional techniques, e.g. filtering or centrifugation, and can be washed and dried. The "drying" encompasses both the removal of the part of the solvent from the isolated solid yielding the solvated form and that of the entire amount of the solvent, thus yielding the solvent-free form. The drying may be performed at ambient or enhanced temperature, at a normal or diminished pressure.

The isolated lenalidomide acid addition salt can, however, be purified if desired. For example, the isolated salt is recrystallized or reprecipitated by dissolving or suspending the isolated salt in a solvent, such as any of the above defined polar solvents, at an enhanced temperature (which includes a reflux temperature of the solvent), and then crystallizing or precipitating the salt from the solvent. The recrystallization (reprecipitation) process may be repeated until a desired purity of the isolated lenalidomide acid addition salt is obtained.

The solid state lenalidomide acid addition salts of the present invention can be advantageously used to obtain purified lenalidomide. Lenalidomide, in general, exhibits quite a low solubility in the most of solvents; thus, a possibility to purify the solution thereof is very limited and the process is economically not effective. The present invention provides economically more effective process.

In general, crude lenalidomide can now be purified by converting it to a lenalidomide acid addition salt as defined above and then converting the lenalidomide salt back into lenalidomide base. A first purification process can comprise (i) combining crude lenalidomide base and an acid having a pKa of about 1 or less in a first solvent, preferably a polar solvent, to obtain an acid addition salt of lenalidomide; (ii)

isolating the acid addition salt of lenalidomide in solid state from the first solvent; (iii) converting the lenalidomide acid addition salt into lenalidomide base in a second solvent, preferably an aqueous solvent; and (iv) isolating the lenalidomide base from said second solvent. This process is particularly useful for removal of impurities, which are soluble in the polar solvent used to form the salt; these impurities generally remain in the first solution during the isolation of the solid lenalidomide acid addition salt; thereby separating these impurities from the lenalidomide moiety. The conversion back to lenalidomide base, especially in an aqueous based solvent, can likewise provide a further purification effect with respect to water-soluble impurities. "Crude lenalidomide" means lenalidomide of insufficient purity and includes reaction mixtures obtained after the chemical synthesis of lenalidomide base, as well as lenalidomide base having near pharmaceutical grade purity.

While the above purification process starts with crude lenalidomide base, it is contemplated that any salt form of a crude lenalidomide could also be used.

Moreover, the isolated acid addition salt of lenalidomide can itself be purified, such as by (re)crystallization as described above, before being converted to lenalidomide base.

The "first solvent" is generally a polar solvent as described above in the context of making the lenalidomide acid addition salts. Thus, examples of suitable first solvents include water, dimethyl sulfoxide, C3-C10 aliphatic ketones (e.g., acetone, methyl tert.butyl ketone, etc.), C1-C6 aliphatic alcohols (e.g., methanol, ethanol, isopropanol), C2-C5 aliphatic nitriles (e.g., acetonitrile), C3-C10 aliphatic or cyclic amides (e.g., N,N-dimethyl formamide, N,N-dimethyl acetamide) as well as mixtures thereof.

The lenalidomide acid addition salt is conveniently isolated as a solid from the first solvent by known techniques such as filtration, etc. The precipitation of the solid state acid addition salt of lenalidomide can be carried out by the techniques as described above.

The isolated solid lenalidomide acid addition salt can be converted into lenalidomide base by any suitable or convenient hydrolysis. Generally, the solid salt is dissolved and/or suspended in the second solvent and an equivalent amount of a base or more is added thereto. The "second solvent" is advantageously an aqueous based solvent in which lenalidomide base is insoluble. Such solvents include water as well as water miscible solvents and combinations thereof. The second solvent is preferably more polar than the first solvent. The base used to convert the salt of lenalidomide to lenalidomide base may be an organic or inorganic base and is preferably a base that binds the acid moiety present in the second solvent to form a salt that is soluble in the second solvent. Suitable bases include sodium and potassium hydroxide. Upon addition of the base to the salt-containing second solvent, lenalidomide generally precipitates in a solid form, preferably as a hydrate (e.g., hemihydrate) when sufficient water is present. The precipitated and purified lenalidomide can then be isolated from the reaction mixture, e.g., by filtration or centrifugation, and is optionally washed and dried. The drying may be performed at ambient or enhanced temperature, at a normal or diminished pressure, to yield a solvent-free form, a hydrated form or a solvated form of lenalidomide base.

A second purification process may comprise the steps of (i) combining crude lenalidomide base and an acid having a pKa of about 1 or less in a solvent, preferably a polar solvent, to obtain a solution of an acid addition salt of lenalidomide; (ii) optionally, filtration of the mixture of the step (i), preferably with the aid of a surface active material; (iii) converting the solution of the lenalidomide acid addition salt into lenalidomide base; and (iv) isolating the lenalidomide base.

This second purification process is useful for removal less polar impurities, particularly those that do not form acid addition salts. The "solvent" employed in this process is generally water, and/or mixtures thereof with water miscible polar organic solvents, e.g. with aliphatic alcohols such as methanol or ethanol or with aliphatic ketones such as acetone or methylethylketone. The filtration in the step (ii) is preferably performed at enhanced temperature, e.g. from 30 degrees Celsius to a temperature close to the boiling point. The surface active material is advantageously the activated carbon. The conversion of the acid addition salt of lenalidomide in the solution to the lenalidomide base as well as the isolation of the lenalidomide base form the reaction mixture is performed substantially as disclosed above at the first purification process.

The acid addition salts of lenalidomide of the present invention can also be formulated in pharmaceutical compositions. For instance, a suitable pharmaceutical composition may comprise a lenalidomide acid addition salt, e.g. lenalidomide hydrochloride, lenalidomide methane sulfonate, lenalidomide benzene sulfonate or lenalidomide p-toluene sulfonate, and at least one pharmaceutically acceptable excipient.

Pharmaceutically acceptable excipients are known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, sugars, etc. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Carbopol® (B.F. Goodrich), Eudragit® (Rohm), polycarbophil, and chitosan polymers. Waxes include white beeswax, microcrystalline wax, carnauba wax, hydrogenated castor oil, glyceryl behenate, glyceryl palmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches. Diluents include water, alcohols, glycerin, dimethyl sulfoxide and combinations thereof.

The pharmaceutical compositions may be formulated into various types of dosage forms. Typical are solid oral dosage forms such as tablets, pellets or capsules; advantageously, however, liquid dosage forms, inclusive injectable solutions, are particularly useful due to the fact that the salts of the invention are, contrary to the lenalidomide base, water soluble.

The pharmaceutically useful single dose of the lenalidomide acid addition salt in the pharmaceutical compositions comprising them may be from 1 to 100 mg and typically comprises 5, 10, 15 or 25 mg, calculated as lenalidomide base.

The lenalidomide acid addition salts of the present invention and pharmaceutical compositions and dosage forms comprising them are useful preferably in treating various blood disorders, such as multiple myeloma or myelodysplasic syndrome by administering an effective amount thereof to a patient in need of such treatment. Typically effective amounts range from 1 to 100 mg and typically comprise 5, 10, 15 or 25 mg, calculated as lenalidomide base and may be administered in one or two portions per day.

The invention will be further described with reference to the following non-limiting examples.

Example 1

Preparation of Lenalidomide Benzene Sulfonate 800 mg of lenalidomide and 536 mg of benzenesulphonic acid were dissolved in 38 ml of a 9/1 mixture of methanol/water while heating. The clear solution was cooled to room temperature then stored at 4° C. over weekend. The suspension was then stored at −20° C. for 4 hours. The formed solid was filtered off, washed once with ether then dried at 40° C. under vacuum over night.

According to NMR, the product exhibits lenalidomide and benzene sulphonic acid moieties in 1:1 molar ratio. DSC showed an endotherm with an onset temperature of 95° C. (the result of evaporation of water as was confirmed with TGA, mass loss 2.1 corresponding to 0.5 equivalent of water) and a melting peak with an onset temperature of 251° C.

Example 2

Preparation of Lenalidomide P-Toluene Sulfonate 800 mg of lenalidomide and 643 mg of toluenesulphonic acid monohydrate were dissolved in 38 ml of a 9/1 mixture of methanol/water while heating. The clear solution was cooled to room temperature then stored at 4° C. over weekend. The suspension was then stored at −20° C. for 4 hours. The formed solid was filtered off, washed once with ether then dried at 40° C. under vacuum over night.

According to NMR, the product exhibits lenalidomide and benzene sulphonic acid moieties in 1:1 molar ratio. DSC showed an endotherm with an onset temperature of 80° C. (the result of evaporation of water as was confirmed with TGA, mass loss 2.2% corresponding to 0.5 equivalent of water) and a melting peak with an onset temperature of 248° C.

The invention having been described it will be obvious that the same may be varied in many ways and all such modifications are contemplated as being within the scope of the invention as defined by the following claims.

The invention claimed is:

1. An acid addition salt of lenalidomide, wherein said salt is selected from (i) a crystalline lenalidomide benzenesulfonate having a ratio of lenalidomide to benzensulfonic acid moiety of about 1:1 and having a melting onset temperature, measured using DSC, of 251° C., or, (ii) a crystalline lenalidomide p-toluenesulfonate having a ratio of lenalidomide to p-toluenesulfonic acid moiety of about 1:1 and having a melting onset temperature, measured using DSC, of 248° C.

2. A process of making an acid addition salt of lenalidomide, which comprises:
   (i) combining lenalidomide base and an acid selected from benzensulfonic acid and p-toluenesulfonic acid in a solvent to form a solution;
   (ii) precipitating a lenalidomide acid addition salt from said solution; and
   (iii) optionally isolating the precipitated lenalidomide acid addition salt;
   wherein said precipitated lenalidominde acid addition salt is a crystalline lenalidomide benzenesulfonate having a ratio of lenalidomide to benzensulfonic acid moiety of about 1:1 and having a melting onset temperature, measured using DSC, of 251° C., or a crystalline lenalidomide p-toluenesulfonate having a ratio of lenalidomide to p-toluenesulfonic acid moiety of about 1:1 and having a melting onset temperature, measured using DSC, of 248° C.

3. A pharmaceutical composition comprising the lenalidomide acid addition salt of the claim 1 and at least one pharmaceutically acceptable excipient.

4. The process according to claim 2, wherein said solvent is a polar solvent.

5. The process according to claim 4, wherein said solvent is a water-alcohol solvent.

6. The acid addition salt according to the claim 1, wherein said salt is a hemihydrate.

* * * * *